United States Patent [19]

Wolf et al.

[11] Patent Number: 5,925,366
[45] Date of Patent: Jul. 20, 1999

[54] NAIL STRENGTHENING COMPOSITIONS AND A METHOD FOR STRENGTHENING NAILS

[75] Inventors: Barbara Ann Wolf, Scarsdale, N.Y.; William Joseph Radice, North Brunswick, N.J.; Teanoosh Moaddel, Woodbridge, N.J.; James Joseph Ferone, Bridgewater, N.J.

[73] Assignee: Revlon Consumer Products Corporation, New York, N.Y.

[21] Appl. No.: 09/084,612

[22] Filed: May 26, 1998

Related U.S. Application Data

[63] Continuation of application No. 08/698,585, Aug. 16, 1996., Pat. No. 5,785,959

[51] Int. Cl.[6] .............................. A61K 6/00; A61K 7/00; A61K 7/025

[52] U.S. Cl. ............................................. 424/401; 424/61
[58] Field of Search ........................................ 424/61, 401

[56] References Cited

U.S. PATENT DOCUMENTS

| | | | |
|---|---|---|---|
| 4,158,053 | 6/1979 | Greene et al. | 424/61 |
| 5,102,654 | 4/1992 | Castrogiovanni et al. | 424/61 |
| 5,472,698 | 12/1995 | Rawlings et al. | 424/401 |

*Primary Examiner*—Thurman K. Page
*Assistant Examiner*—Sharon Howard
*Attorney, Agent, or Firm*—Julie Blackburn

[57] ABSTRACT

A nail strengthening composition comprising, by weight of the total composition:
a) 0.1–60% by weight of a permeation/binding agent,
b) 0.001–20% of a thio cross-linking agent,
c) 0.001–20% of a chelating agent.

11 Claims, No Drawings

NAIL STRENGTHENING COMPOSITIONS AND A METHOD FOR STRENGTHENING NAILS

This is a continuation of application Ser. No. 08/698,585, filed Aug. 16, 1996, now U.S. Pat. No. 5,785,959.

TECHNICAL FIELD

The invention is in the field of compositions for application to finger- and toenails for the purpose of strengthening the nails.

BACKGROUND OF THE INVENTION

The nail is formed by corneocytes that are flattened in a plane and stacked one on top of the other in a "brick-wall" arrangement. Keratin fibrils found within the corneocytes provide strength and flexibility to the cells due to the presence of cystine disulphide bridges, which are found at a level of about 9.4% by weight in the nail. In addition, the intercellular adhesive factors which hold corneocytes together also provide strength and flexibility. These intercellular adhesive factors are: (1) intercellular cement, which contains lipids (2) desmosomes, and (3) gap junctions and narrow junctions.

Brittle, unhealthy nails usually result from some disruption in the normal levels of intercellular adhesive factors. This can occur through nail dehydration, infections, exposure to toxic agents, injuries, and so on.

Compositions for application to nails to effect strengthening are well known in the art. However, since the biology of the nail is not well understood, it has been difficult to formulate compositions which contain ingredients which are capable of interacting with the nail plate to provide a beneficial result. One other problem with current nail strengthening agents is that the user cannot usually apply nail polish on top of the strengthening agent Obviously this poses a disadvantage, since women who are interested in strengthening nails tend to be the same women who wear nail enamel.

There is a need in the art for nail strengthening compositions which contain ingredients which are capable of reacting with the nail itself to provide enhanced results and which are capable of use with or without nail enamel.

SUMMARY OF THE INVENTION

The invention is directed to a nail strengthening composition comprising, by weight of the total composition:
 a) 0.1–60% by weight of a permeation/binding agent,
 b) 0.001–20% of a thio cross-lining agent,
 c) 0.001–20% of a chelating agent.

The invention is also directed to a method for strengthening nails comprising to the nails the above mentioned composition.

DETAILED DESCRIPTION

All percentages mentioned herein are percentages by weight unless otherwise indicated. The composition of the invention contains three essential components.

The Permeation/Binding Agent

The composition of the invention contains 0.1–60%, preferably 0.1–25%, most preferably 0.5–15% of a permeation/binding agent. The permeation/binding agent exhibits dual functionality: it must be capable of being absorbed into the nail and at the same tine it must be capable of, itself, binding water or lipids or both. The permeation/binding agent generally has a molecular weight of less than 2,000, preferably less than 1,000 daltons. Permeation binding agents that bind water, or water permeation/binding agents will be capable of binding water from the environment, from the living tissue below the nail, or nail bed, or from water that may be applied to the nail, thus promoting retention of water within the nail. The normal nail contains from about 7–18% water. Although the nail is capable of absorbing up to about 30% water, it does not "hold on" to water effectively. The low water content of nail is what causes nail hardness. However, if the water content of the nail is too low the result is excessively hard, or brittle nails. The water permeation/binding agent will be generally soluble in water at 40° C. The water permeation/binding agent is capable of binding water molecules by hydrogen bonding. Examples of water permeation/binding agents include hydroxycarboxylic acids such as those disclosed in U.S. Pat. No. 5,470,880, which is hereby incorporated by reference. Such hydroxycarboxylic acids include hydroxymonocarboxylic acids having the general formula:

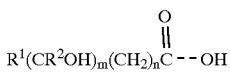

wherein $R^1$ and $R^2$ are H, alkyl, aralkyl, or aryl groups of saturated or unsaturated straight or branched chain or cylic form having 1 to 25 carbon atoms, m is 1–9, and n is 0–23. Examples of hydroxymonocarboxylic acids include aldonic acid, glycolic acid, lactic acid, methyllactic acid, 2-hydroxybutanoic acid, mandelic acid, atrolactic acid, phenyllactic acid, glyceric acid, 2,3,4-trihydroxybutanoic acid, 2,3,4,5-tetrahydroxypentanoic acid, 2,3,4,5,6-pentahydroxyhexanoic acid, alpha hydroxylauric acid, benzilic acid, 4-hydroxymandelic acid, aleuritic acid, and the like. The hydroxymonocarboxylic acid may exist in the free acid, lactone, salt, ester, or amide form.

The hydroxycarboxylic acid may also be a hydroxydicarboxylic acid, such as tartaric acid, malic acid, erythraric acid, threaric acid, arabiraric acid, ribaric acid, xylaric acid, and lyxaric acid, glucaric acid, galactaric acid, mannaric acid, gluaric acid, allaric acid, altraric acid, idaric acid and talaric acids. Also suitable are the salt, ester, and amide derivatives of hydroxdicarboxylic acids.

The permeation/binding agent may be a compound that is capable of being absorbed into the nail and binding lipids which are found in the nail, in the living tissues below the nail, or in products which are applied to the nail surface. It is also known that in the nail lipids act as barriers to diffusion of water. The lipids are found mostly as a component of the intercellular cement. The nail contains very low levels of lipids, i.e. in general less than about 5%. This accounts for the general inability of the nail to bind water effectively. It is believed that brittle nails can also be caused by a deficiency of the lipids in the nail, perhaps because the reduced level of lipids further promotes diffusion of water from the nail. A deficiency of lipids in the nail has also been shown to be due to use of organic solvent based nail enamel removers which leach lipids from the nail [*J. Soc. Cosmet Chem.*, Japan, Report, 23(3) 288–294 (1994)]. The lipid permeation/binding agent, once it is absorbed into the nail, will bond lipids via hydrophobic bonds or Van der Waals forces, and will generally become part of the intercellular cement. The increased lipid levels will, in turn, hinder diffusion of water from the nail. Generally the lipid permeation/binding agent is soluble in nonaqueous solvents and insoluble or dispersible in water. Typical examples of lipid permeation/binding agents include saturated and unsaturated fatty acids such as lauric, myristic, palmitic, stearic, oleic, linoleic, linolenic, acids, and so on. Also suitable as the lipid permeation/binding agent are fatty alcohols having the formula RCOOH wherein R is a 8–20 straight or branched chain saturated or unsaturated alkyl. Also suitable are triglycerides, acylceramides, cholesterol, squalene, glyceryl esters, ceramides, linoleamidorpopyl PG dimonium chloride, glycoceramides, sphingolipids, and so on.

The permeation/binding agent may be capable of binding both water and lipids. These molecules generally have polar and nonpolar portions and may be soluble or insoluble in water depending on the level of polar and nonpolar substituents in the molecule. The preferred permation/binding agent is one that is capable of binding both water and lipid, such as N-alkoxyalkylamides as disclosed in U.S. Pat. No. 5,084,270, which is hereby incorporated by reference. These N-alkoxyalkylamides have the general formula:

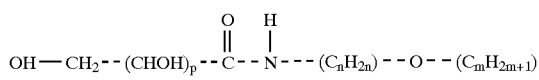

wherein p is a whole number from 1 to 4, $C_nH_{2n}$ is a straight or branched chain alkyl bridge in which n is a whole number of 1 to 6, and preferably 1–4, and more preferably 3, and $(C_mH_{2m+1})$ is a straight or branched chain alkylene group in which m is a whole number of 1 to 6, preferably 1 to 4, and more preferably 1. Most preferred is a compound of the above formula where p=4, n=3, and m=1, which is methoxypropylgluconamide.

Another suitable permeation/binding agent capable of binding both water and lipids are alkyl diamides disclosed in U.S. Pat. No. 5,139,784, which is hereby incorporated by reference. These alkyl diamides have the following general formula:

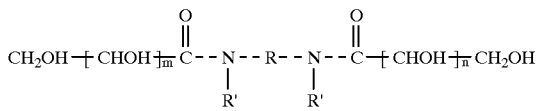

wherein m and n are independently whole numbers from 0 to about 4, R is a substituted or unsubstituted hydrocarbon selected from the group consisting of aryl and alkyl radicals containing from about 2 to about 14 carbon atoms and each R' is independently hydrogen or a $C_{1-4}$ alkyl. Preferred is wherein each R' is hydrogen and R is a hydrocarbon selected from the group consisting of aryl and alkyl radicals containing from about 2 to 14 carbon atoms. Most preferred are bisgluconamides, and particularly N,N-1,3-propanediol-2-hydroxybisgluconamide which has the following formula:

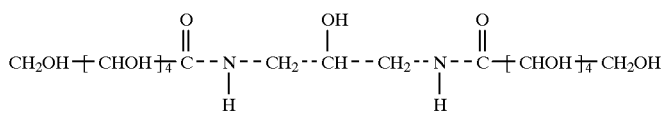

Ideally the permeation/binding agent should bind both water and lipids, or the composition of the invention should contain a mixture of water and lipid permeation/binding agents so that water which is introduced into the nail can be retailed there and not lost due to reduced lipid barrier function.

The Thio Cross Linking Agent

The composition of the invention contains 0.001–20%, preferably 0.01–15%, more preferably 0.01–10% of a thio cross-linking agent. The term "thio cross-linking agent" means that the cross-linking agent contains thio groups which are capable of reacting with the free cysteine, or cystine-like molecules found within the nail protein. Such compounds may have free SH groups, or contain S—S linkages which are easily hydrolyzed to produce free thiol or mercaptide groups, thus permitting binding of the cross linking agent to cystine or similar compounds within the nail. Typical examples of thio cross-linking agents include thioctic acid, ammonium thioglycolate, ammonium thiolactate, biotin, bispyrithione, calcium thioglycolate, carbocysteine, cobalt acetylmethionate, copper acetylmethionate, cysteamine hydrochloride, cysteine, cysteine hydrochloride, glutathione, cystine, decyl mercaptomethylimidazole, diammonium dithiodiglycolate, dibenzothiophene, dicapryloyl cystine, dicetyl thiodipropionate, lilauryl thiodipropionate, dimethylol ethylene thiourea, dimethyl sulfone, dimyristyl thiodipropnionate, dipalmitoyl cystine, distearyl thiodipropionate, dithiodiglycolic acid, ditridecyl thiodipropionate, ethanolamine dithiodiglycolate, ethanolanine thioglycolate, glyceryl thioglycolate, isooctyl thioglycolate, mecraptopropionic acid, methionine, methylsilanol acetymethionate, nickel acetylmethionate, pantethine, PEG-6 isolauryl thioether, PEG-8 isolauryl thioether, PEG-10 isolauryl thioether, phenylthioglycolic acid, potassium thioglycolate, silver acetylmethionate, sodium pyrithione, sodium thioglycolate, sulfurized jojoba oil, thenoyl methionate, thiamine hydrochloride, thiamine nitrate, 2,2'-thiobis(4-chlorophenol), thiodiglycol, thiodiglycolamide, thiodiglycolic acid, thioglycerin, thioglycolic acid, thiolanediol, thiosalicylic acid, zinc acetylmethionate, and so on. Preferred are thioctic acid, pantetheine, biotin, glutathione, and mixtures thereof.

The Chelating Agent

The composition also contains 0.001–20%, preferably 0.01–15%, more preferably 0.01–10% of a chelating agent It is believed that brittle nails may also be caused by an excess of calcium in the nail. It may be that the nail itself acts as an ion-exchange resin and absorbs calcium from the environment [Rieger, Cosmetics & Toileties, Vol. 97, 1982, pp. 33–35]. The chelating agent will complex with calcium in the nail, thereby inactivating the calcium and preventing it from promoting excessive nail hardness. Suitable chelating agents include aminotrimethylene phosphonic acid, calcium disodium EDTA, cyclodextrin, cyclohexanediamine tetraacetic acid, diammonium citrate, diammonium EDTA, dipotassium EDTA, disodium EDTA, disodium pyrophosphate, EDTA, etidronic acid, HEDTA, methyl cylodextrin, pentapotassium triphosphate, pentasodium aminotrimethylene phosphate, pentasodium pentetate, pentasodium triphosphate, pentetic acid, sodium azacycloheptane diphosphonate, sodium dihydroxyethylglycinate, sodium gluconate, sodium glycereth-1 polyphosphate, sodium hexametaphosphate, sodium metaphosphate, sodium metasilicate, sodium polydimethylglycinophenolsulfonate, sodium trimetaphosphate, TEA-EDTA, tetrahydroxyethyl ethylenediamine, tetrahydroxypropyl ethylenediamine, tetrapotassium pyrophosphate, tetrasodium EDTA, tetrasodium etidronate, tetrasodium pyrophosphate, tripotassium EDTA, trisodium EDTA, trsodium EDTA, trisodium HEDTA, trisodium NTA, trisodium phosphate, phytic acid, EGTA, and mixtures thereof. Preferred are EDTA and derivatives therof.

Other Ingredients

The compositions of the invention may also contain other ingredients such as water, oil, vitamins, humectants, pigments or colorants, thickeners, emulsifiers, preservatives, fragrances, and the like.

Oils may be present, if desired, and suitable ranges are 0.1–60%, preferably 1–50%, more preferably 5–40% oil. Suitable oils include volatile and nonvolatile silicones. The term "volatile" means that the silicone has a vapor pressure of at least 2 mm. of mercury at 20° C. The term "nonvolatile" means that the silicone has a vapor pressure of less than 2 mm. of mercury at 20° C. Suitable volatile silicones may be linear or cyclic. Cyclic volatile silicones have the general formula:

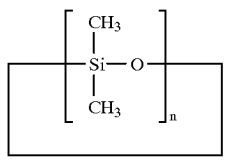

wherein n=3–7, preferably 3–6.

Also suitable are volatile and nonvolatile linear silicones having the general formula.

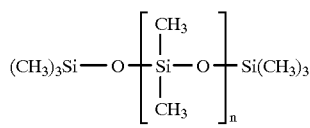

wherein n=0–1,000,000. Examples of such silicones include cyclomethicone, hexamethyldisiloxane, dimethicone, and the like.

Also suitable are silicone surfactants such as dimethicone copolyol, dimethiconol, and the like, as well as phenyl substituted silicones like phenyl trimethicone, phenyl dimethicone, and so on.

Volatile and nonvolatile paraffinic hydrocarbon fluids such as mineral oil, or $C_{5-40}$ straight or branched chain hydrocarbon fluids are also suitable for the oil ingredient. Examples of volatile paraffinic hydrocarbon fluids are disclosed in U.S. Pat. Nos. 3,439,088 and 3,818,105 which are hereby incorporated by reference. Such paraffinic hydrocarbons include isododecane, isohexadecane, decane, dodecane, and so, on. These types of paraffinic hydrocarbon fluids are sold by Permethyl under the Permethyl tradename.

Preferred oil ingredients are silicones either alone or in combination with nonvolatile paraffinic hydrocarbon fluids.

Vitamins

It may be desireable to add vitamins, and if so 0.01–20%, preferably 0.1–15%, more preferably 0.1–10% vitamins are suggested. Examples of suitable vitamins include vitamin E (tocopherol) vitamin C PMG (also known as magesium ascorbyl phosphate), thiamine, pyridoxine, nicotinide, vitamin D, or mixtures thereof.

Amines

It may be desireable to add amine compounds which are believed to have a superficial conditioning effect. If amines are added, 0.0001–5%, preferably 0.001–3%, more preferably 0.001–2% is suggested. Suitable amines may be primary, secondary or tertiary, or polyamines. Primary, secondary and tertiary amines exhibit the general formula $RNH_2$, $RR'NH_2$, or $RR'R''NH_2$ respectively wherein R, R', and R'' are $C_{1-50}$ straight or branched chain alkyl; substituted or unsubstituted phenyl where the substitutents are allyl, hydroxyl, halogen, amino; and the like, as well as other amines. Examples of such amines are disclosed on pages 488–490 of the *CTFA Cosmetic Ingredient Handbook*, Second Edition, 1992.

Preferred are polyamines, particularly those having the following general formula:

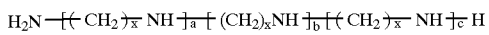

wherein each x is independently 1–10, and a, b, and c are each independently 0–20, with the proviso that at at least one of a, b, or c is 1. Most preferred is a polyamine of the formula:

This polyamine is referred to as spermine.

Humectants

The composition of the invention may also contain 0.01–20%, preferably 0.1–10%, more preferably 0.1–5% humectants. Humectants are ingredients which retard moisture loss, and are generally hygroscopic in nature. Examples of humectants include sugars such as corn syrup, fructose, glucose, glycerin, honey, inositol, maltitol, trehelose, mannitol, sorbitol, sucrose, xylitol, and the like, as well as polyethylene glycols, and derivatives thereof, butylene glycol, ethylene glycol, urea, and so on.

Emulsifiers

The composition of the invention may also contain 0.01–10% preferably 0.01–8%, more preferably 0.1–5% of an emulsifier. Suitable emulsifiers include alkoxylated alcohols such as laura, ceteth, deceth, pareth, oleth, steareth, and so on. Also suitable are polyethylene glycol derivatives of fatty acids, poloxamers, polyglyceryl derivatives, polysorbates, and the like.

Preservatives

The compositions may contain 0.01–10%, preferably 0.1–8%, more preferably 0.1–5% preservatives. Suitable preservatives include the parabens such as methyl, ethyl, and propyl paraben, benzoic acid, benzyl alcohol, calcium benzoate, DMDM hydantoin, diazolidinyl urea, DMDM hydantoin, methychloroisothiazolinone, quaternary ammonium compounds, and so on.

The nail strengthening composition of the invention may be in the form of a water-in-oil or oil-in-water emulsion. In the alternative, it may be found in the anhydrous form, or as part of a nail enamel composition.

It is preferred that the composition of the invention is a water-in-oil or oil-in-water emulsion which is applied to the nail either alone or before application of nail enamel. Such composition comprises:

a) 0.1–0% by weight of a permeation/binding agent, b) 0.001–20% of a thio cross-linking agent, c) 0.001–20% of a chelating agent, d) 5–80% water, e) 1–60% oil.

In addition, the preferred composition contains 0.001–5% of an amine conditioning agent, preferably a polyamine.

Particularly preferred is a nail strengthening composition containing:

0.5–15% of a permeation/binding agent which is an N-alkoxyalkylamide, 0.01–15% of a thio cross-linking agent which is thioctic acid, biotin, pantetheine, or mixtures thereof, 0.01–10% of a chelating agent, 5–80% water, 1–50% of an oil, 0.001–5% of a polyamine conditioning agent, 0.01–20% of a humectant, 0.01–8% of an emulsifier.

Preferably the oil is silicone oil and the emulsifier is one or more alkoxylated alcohols.

EXAMPLE 1

A nail strengthening composition was made according to the following formula:

|  | w/w % |
|---|---|
| Water | 60.21 |
| Citric acid | 0.05 |
| Glycerin | 5.00 |
| Magnesium ascorbyl phosphate | 0.05 |
| EDTA | 0.05 |
| Butylene glycol | 5.00 |
| Ethyl paraben | 0.20 |
| Methyl paraben | 0.30 |
| Xanthan gum | 0.25 |
| Magnesium aluminum silicate | 0.70 |
| Folic acid | 0.01 |
| Steareth-20 | 0.20 |
| Steareth-2 | 0.20 |
| Cetyl alcohol | 0.65 |
| Cyclomethicone | 12.00 |
| Glyceryl stearate | 0.25 |
| Propylene glycol dicaprylate/dicaprate | 4.00 |
| Stearyl alcohol | 0.55 |
| Tocopherol | 0.025 |
| Dimethicone | 2.50 |
| Urea | 0.30 |
| Methoxypropylgluconamide | 5.00 |
| Sodium hyaluronate/glycosaminoglycans | 0.10 |
| Methoxypropylgluconamide/glyceryl distearate | 0.50 |
| Thioctic acid | 1.50 |
| Pantetheine | 2.00 |
| Linoleamidopropyl-PG dimonium chloride | 1.00 |
| Pyridoxine | 0.10 |
| Biotin | 0.01 |
| Spermine | 0.01 |

EXAMPLE 2

A solvent based nail strengthening/enamel composition is made as follows:

|  | w/w % |
|---|---|
| Nitrocellulose | 17.7 |
| Butyl acetate | 27.2 |
| Ethyl acetate | 27.0 |
| Isopropyl alcohol | 8.0 |
| Glyceryl tribenzoate | 13.1 |
| Linoleic acid | 4.8 |
| Phytic acid (10% solution in ethyl alcohol) | 0.1 |
| Thiooctic acid | 0.1 |
| Stearalkonium bentonite | 1.0 |
| 2,5 dibutyl pheny 3,5 di t-butyl-4-hydroxy benzoate | 1.0 |

EXAMPLE 3

An aqueous nail strengthening/enamel composition is made as follows:

|  | w/w % |
|---|---|
| Aqueous acrylic emulsion[1] | 71.0 |
| Water | 6.25 |
| Isopropyl alcohol | 4.1 |
| Coalescent[2] | 14.9 |
| Plasticizer[3] | 1.5 |
| Phytic acid (10% solution in ethyl alcohol) | 0.1 |
| Thiooctic acid | 0.5 |
| Linoleic acid | 0.4 |
| Preservatives | 0.25 |

[1]Rhoplex WL 81, Rohm & Haas Co.
[2]Dipropylene glycol methyl ether and dipropylene glycol t-butyl ether, Arco Chemical Co.
[3]Paraplex WP-1, Rohm & Haas Co.

We claim:

1. A nail strengthening composition in the form of a non-aqueous solvent based nail enamel containing a nitrocellulose film forming agent, comprising, by weight of the total composition:

a) 0.1–60% of a permeation/binding agent, b) 0.001–20% of a thio cross-linking agent, c) 0.001–20% of a chelating agent.

2. The composition of claim 1 wherein the solvent is selected from the group consisting of butyl acetate, ethyl acetate, isopropyl alcohol, and mixtures thereof.

3. The composition of claim 1 wherein the permeation/binding agent is a water permeation/binding agent, a lipid permeation/binding agent, or mixtures thereof.

4. The composition of claim 3 wherein the water permeation/binding agent is an alpha hydroxy acid; a beta hydroxy acid; an ester, amide or salt derivative of an alpha hydroxy acid; an ester, amide or salt derivative of a beta hydroxy acid; or an N-alkoxyalkylamide.

5. The composition of claim 3 wherein the lipid permeation/binding agent is a fatty acid, a fatty alcohol, triglycerides, acylceramides, cholesterol, squalene, glyceryl esters, ceramides, linoleamidopropyl PG dimonium chloride, and mixtures thereof.

6. The composition of claim 4 wherein the permeation/binding agent is an N-alkoxyalkylamide of the formula:

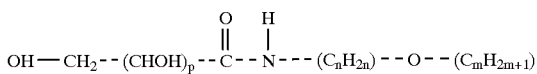

wherein p is a whole number from 1 to about 4, $(C_nH_{2n})$ is a straight or branched chain alkyl bridge in which n is a whole number of 1 to 6, and $(C_mH_{2m+1})$ is a straight or branched chain alkyl group in which m is a whole number of 1 to 6.

7. The composition of claim 6 wherein the water permeation/binding agent is methoxypropylgluconamide.

8. The composition of claim 1 wherein the thio crosslinking agent is thioctic acid, ammonium thioglycolate, ammonium thiolactate, biotin, bispyrithione, calcium thioglycolate, carbocysteine, cobalt acetylmethionate, copper acetylmethionate, cysteamine hydrochloride, cysteine, cysteine hydrochloride, cystine, decyl mercaptomethylimidazole, diammonium dithiodiglycolate, dibenzothiophene, dicapryloyl cystine, dicetyl thiodipropionate, lilauryl thiodipropionate, dimethylol ethylene thiourea, dimethyl sulfone, dimyristyl thiodipropnionate, dipalmitoyl cystine, distearyl thiodipropionate, dithiodiglycolic acid, ditridecyl thiodipropnionate, ethanolamine dithiodiglycolate, ethanolamine thioglycolate, glyceryl thioglycolate, isooctyl thioglycolate, mercaptopropionic acid, methionine, methylsilanol acetymethionate, nickel acetylmethionate, pantethine, PEG-6 isolauryl thioether, PEG-8 isolauryl thioether, PEG-10 isolauryl thioether, phenylthioglycolic acid, potassium thioglycolate, silver acetylmethionate, sodium pyrithione, sodium thioglycolate, sulfurized jojoba oil, thenoyl methionate, thiamine hydrochloride, thiamine nitrate, 2,2'-thiobis(4-chlorophenol), thiodiglycol, thiodiglycolamide, thiodiglycolic acid, thioglycerin, thioglycolic acid, thiolanediol, thiosalicylic acid, glutathione, zinc acetylmethionate, and mixtures thereof.

9. The composition of claim 8 wherein the thio crosslinking agent is selected from the group consisting of thioctic acid, pantetheine, biotin, and mixtures thereof.

10. The composition of claim 1 wherein the chelating agent is aminotrimethylene phosphonic acid, calcium disodium EDTA, cyclodextrin, cyclohexanediamine tetraacetic acid, diammonium citrate, diammonium EDTA, dipotassium EDTA, disodium EDTA, disodium pyrophosphate, EDTA, etidronic acid, HEDTA, methyl cyclodextrin, pentapotassium triphosphate, pentasodium aminotrimethylene phosphate, pentasodium pentetate, pentasodium triphosphate, pentetic acid, sodium azacycloheptane diphosphonate, sodium dihydroxyethylglycinate, sodium gluconate, sodium glycereth-1 polyphosphate, sodium hexametaphosphate, sodium metaphosphate, sodium metasilicate, sodium polydimethylglycinophenolsulfonate, sodium trimetaphosphate, TEA-EDTA, tetrahydroxyethyl ethylenediamine, tetrahydroxypropyl ethylenediamine, tetrapotassium pyrophosphate, tetrasodium EDTA, tetrasodium etidronate, tetrasodium pyrophosphate, tripotassium EDTA, trisodium EDTA, trisodium EDTA, trisodium HEDTA, trisodium NTA, trisodium phosphate, phytic acid, EGTA, and mixtures thereof.

11. The composition of claim 10 wherein the chelating agent is EDTA or a derivative thereof.

* * * * *